(12) United States Patent
Antognozzi et al.

(10) Patent No.: US 12,405,271 B2
(45) Date of Patent: Sep. 2, 2025

(54) METHOD AND APPARATUS FOR BACTERIAL ANALYSIS

(71) Applicant: The University of Bristol, Bristol (GB)

(72) Inventors: Massimo Antognozzi, Bristol (GB); Charlotte Bermingham, Bristol (GB); Krishna Coimbatore Balram, Bristol (GB); Ruth Oulton, Bristol (GB)

(73) Assignee: The University of Bristol, Bristol (GB)

( * ) Notice: Subject to any disclaimer, the term of this patent is extended or adjusted under 35 U.S.C. 154(b) by 526 days.

(21) Appl. No.: 16/634,449

(22) PCT Filed: Jul. 30, 2018

(86) PCT No.: PCT/GB2018/052154
§ 371 (c)(1),
(2) Date: Jan. 27, 2020

(87) PCT Pub. No.: WO2019/025771
PCT Pub. Date: Feb. 7, 2019

(65) Prior Publication Data
US 2021/0088513 A1    Mar. 25, 2021

(30) Foreign Application Priority Data

Jul. 31, 2017  (GB) .................................... 1712279

(51) Int. Cl.
*G01N 33/543*    (2006.01)
*A61L 2/025*    (2006.01)
(Continued)

(52) U.S. Cl.
CPC ........ *G01N 33/54373* (2013.01); *A61L 2/025* (2013.01); *C12M 1/3446* (2013.01);
(Continued)

(58) Field of Classification Search
CPC ............. G01N 33/54373; G01N 21/49; G01N 21/552; G01N 21/7703; G01N 33/56911;
(Continued)

(56) References Cited

U.S. PATENT DOCUMENTS 3,772,154 A    11/1973 Isenberg et al.
4,703,182 A * 10/1987 Kroneis ............... G01N 21/645
250/365

(Continued)

FOREIGN PATENT DOCUMENTS

EP    0959343 A1 * 11/1999
EP    0700514 B1 * 11/2001
(Continued)

OTHER PUBLICATIONS

Edwards et al., "Fiber taper based Raman spectroscopic sensing", IEEE, 2012, 501-502 (Year: 2012).*
(Continued)

*Primary Examiner* — Henry H Nguyen
(74) *Attorney, Agent, or Firm* — Hunton Andrews Kurth LLP

(57) ABSTRACT

An apparatus (10) comprising: a light source (12); to cast light toward a substrate (20) defining a bacteria binding volume to create an evanescent field (22), the bacteria binding volume being within the evanescent field; a detector (32, 34) arranged to receive light from the bacteria binding volume and output data (36, 37); and a processor (38) arranged to determine vibration of bacteria (26) with the bacteria binding volume in three-dimensions from the data.

16 Claims, 1 Drawing Sheet

(51) Int. Cl.
  *C12M 1/34* (2006.01)
  *C12Q 1/00* (2006.01)
  *G01N 21/49* (2006.01)
  *G01N 21/55* (2014.01)
  *G01N 21/552* (2014.01)
  *G01N 21/77* (2006.01)
  *G01N 33/569* (2006.01)

(52) U.S. Cl.
  CPC ............... *C12Q 1/00* (2013.01); *G01N 21/49* (2013.01); *G01N 21/552* (2013.01); *G01N 21/7703* (2013.01); *G01N 33/56911* (2013.01); *G01N 2021/556* (2013.01)

(58) Field of Classification Search
  CPC ..... G01N 2021/556; G01N 2021/4709; G01N 21/553; A61L 2/025; C12M 1/3446; C12Q 1/00
  See application file for complete search history.

(56) References Cited

U.S. PATENT DOCUMENTS

| | | | |
|---|---|---|---|
| 2002/0016011 A1* | 2/2002 | Perkins | G01N 21/648 436/524 |
| 2002/0094528 A1* | 7/2002 | Salafsky | G01N 33/54373 435/6.12 |
| 2007/0117217 A1* | 5/2007 | Lal | G01N 33/6854 436/513 |
| 2007/0281331 A1* | 12/2007 | Koo | G06T 7/20 382/128 |
| 2008/0131315 A1* | 6/2008 | Takase | G01N 21/78 422/52 |
| 2009/0304551 A1* | 12/2009 | Mutharasan | G01N 21/7703 422/82.11 |
| 2012/0202194 A1* | 8/2012 | Evers | G01N 15/1434 435/5 |
| 2015/0168300 A1* | 6/2015 | Peterson | G02B 21/00 356/445 |
| 2017/0045514 A1 | 2/2017 | Tao et al. | |
| 2017/0205612 A1* | 7/2017 | Carloni | G01N 21/648 |
| 2018/0321152 A1* | 11/2018 | Nagai | G01N 21/6428 |

FOREIGN PATENT DOCUMENTS

| | | |
|---|---|---|
| WO | 1998/22808 A1 | 5/1998 |
| WO | 2004/031743 A1 | 4/2004 |
| WO | 2004/061434 A1 | 7/2004 |
| WO | 2007/077218 A1 | 7/2007 |
| WO | 2008/122799 A1 | 10/2008 |
| WO | 2008122800 A1 | 10/2008 |
| WO | 2008156560 A1 | 12/2008 |
| WO | 2010/123900 A1 | 10/2010 |
| WO | 2011/066097 A1 | 6/2011 |
| WO | 2012/074805 A1 | 6/2012 |
| WO | WO-2016096901 A1 * | 6/2016 ........... C12Q 1/6825 |

OTHER PUBLICATIONS

Zibaii et al., "Measuring bacterial growth by refractive index tapered fiber optic biosensor", Journal of Photochemistry and Photobiology B: Biology, 2010, 313-320 (Year: 2010).*

Chiu et al., "Functioning Nanomachines Seen in Real-Time in Living Bacteria Using Single-Molecule and Super-Resolution Fluorescence Imaging", 2011, Int. J. Mol., Sci, 12(4), 2518-2542 (Year: 2011).*

Machine translation of EP0959343A1, Kunz Rino, Nov. 24, 1999 (Year: 1999).*

Delalez et al, "Signal-dependent turnover of the bacterial flagellar switch protein FliM", 2010, PNAS, vol. 107, No. 25, 11347-11351 (Year: 2010).*

Maximilian Kloucek et al., "Detecting Metabolic Activity of Living Bacteria Using Evanescent Waves," URC/IAS Undergraduate Interdisiplinary Research Internship Schme (IRIS) 2016, Nov. 22, 2016, p. 1.

Kim Van Ommering et al., "Mobility and Height Detection of Particle Labels in an Optical Evanescent Wave Biosensor With Single-Label Resolution," Journal of Physics D: Applied Physics Institute of Physics Publishing Ltd., GB, vol. 43, No. 15, Apr. 21, 2010, pp. 1-8.

UK Intellectual Property Office, Combined Search and Examination Report Under Sections 17 and 18(3), May 18, 2018, pp. 1-7.

International Searching Authority, PCT International Search Report and Written Opinion, Sep. 27, 2018, pp. 1-16.

* cited by examiner

METHOD AND APPARATUS FOR BACTERIAL ANALYSIS

This application is a U.S. national phase application under 35 U.S.C. § 371 of International Application No. PCT/GB2018/052154, filed Jul. 30, 2018, which claims priority to U.K. Application No. 1712279.7 filed Jul. 31, 2017, the complete disclosure of which is incorporated herein by reference.

BACKGROUND OF THE INVENTION

Recently, the rise in antimicrobial resistance has become problematic for the treatment of bacterial infections. There is therefore a need for antimicrobial resistance to be detected more rapidly and at lower cost.

SUMMARY OF THE INVENTION

A first aspect of the invention provides an apparatus comprising: a light source arranged to cast light toward a substrate defining a bacteria binding volume to create an evanescent field and the bacteria binding volume is within the evanescent field; a detector arranged to receive light from the bacteria binding volume and output data; and a processor arranged to determine a level of vibration of bacteria within the bacteria binding volume in three-dimensions from the data.

With such an arrangement, there is provided a simpler apparatus for detecting antimicrobial resistance.

The light from the bacteria binding volume can be any light which contains information regarding the level of vibration of the bacteria. This can be light which has been scattered by bacteria due to their movement in the evanescent field and/or can be light which has been totally internally reflected and so has the profile of the incident light except that the light lacks the photons which are in the scattered light.

The light source may be a laser light source. With such an arrangement, the evanescent field can be created more reliably.

The apparatus may further comprise a lens arranged to direct the light from the light source towards the substrate. With such an arrangement, the evanescent field can be produced by light arriving at an angle closer to the critical angle.

The lens may be a high numerical aperture lens, having a numerical aperture of 1.4 or more, such as 1.41. With such an embodiment, the evanescent field can be produced with a sufficiently large size.

The lens may be arranged to receive light from the bacteria binding volume. With such an arrangement, the light from the bacteria binding volume can be directed toward the detector without the use of a greater number of lenses.

The detector may be a quadrant photodiode detector. With such an arrangement, the movement of the bacteria in four different sectors can be determined in order that the vibration of the bacteria in the binding volume can be measured more precisely.

The determined vibration may be of a single bacterium. With such an arrangement, no culturing of bacteria is required so that the overall process of determining antimicrobial resistance can be made more rapidly.

The apparatus may further comprise a coverslip arranged to support the bacteria binding volume. With such an arrangement, there is provided a transparent support for the bacteria binding volume so that the evanescent field may be created without light from the light source travelling through the bacteria binding volume.

The light source and lens may be arranged to cause the light to undergo total internal reflection on the surface of the coverslip. With such an arrangement, the evanescent field can be correctly positioned to contain bacteria bound by the bacteria binding volume.

The evanescent field may be created on the surface of the coverslip. With such an arrangement, the evanescent field is correctly positioned to be affected by vibrations of bacteria bound within the bacteria binding volume.

The evanescent field may have a decay length of no more than two hundred nanometres. With such an arrangement, the evanescent field will not extend far past the bacteria, in order that the scattering of light can be caused by the bacteria only.

The first detector may be arranged to receive light scattered by the bacteria in the binding volume. With such an arrangement, the bacteria can be analysed with less processing.

The apparatus may further comprise a second detector arranged to receive light from the light source having undergone total internal reflection, which is not scattered by the bacteria. With such an arrangement, the second detector can provide a check in order to determine whether the data received from the first detector is correct and may be used to measure the fluctuations of the bacteria.

The apparatus may further comprise a second light source, the second light source being arranged to direct light through the coverslip, the light from the second light source undergoing multiple internal reflections within the coverslip. With such an arrangement, the vibrations of multiple bacteria can be detected in order to give a determination of antimicrobial resistance with the apparatus in use for a shorter time.

The coverslip may be formed of a dielectric material having a refractive index greater than 1.6. With such an arrangement, the total internal reflections can be reliably produced.

The apparatus may further comprise a second light source and an optical waveguide arranged to support the bacteria binding volume, the second light source arranged to direct light through the optical waveguide. With such an arrangement, there is provided an alternative arrangement without use of a coverslip.

The optical waveguide may be tapered at a point within the evanescent field. With such an arrangement, the apparatus can be more sensitive to the vibrations of the bacteria within the evanescent field, having a greater signal-to-noise ratio.

The apparatus may further comprise a CMOS or CCD imaging device arranged to observe the bacteria. With such an arrangement, a manual measurement of the level of vibration can be made in order to check an automated result.

The vibrations within each bacterium may be recorded and stored as video footage. The footage may have a high resolution such that an observer can visually analyse the vibrations. With such an arrangement, the video can be analysed to give a measurement of bacterial activity alternatively or in addition to the measurement obtained from the position sensitive detector.

A further aspect of the invention provides a method comprising: arranging one or more bacteria on a surface of a coverslip; directing light to be totally internally reflected on the surface of the coverslip and thereby creating an evanescent field on the surface of the coverslip, the evanescent field containing the bacteria; detecting light from the evanescent field; and determining a level of vibration of the bacteria from the detected light.

The detected light can be any light which contains information regarding the level of vibration of the bacteria. This can either be light which has been scattered by bacteria due to their movement in the evanescent field or can be light which has been totally internally reflected and so has the profile of the incident light except that the light lacks the photons which are in the scattered light.

With such an arrangement, there is provided a more simple method for determining antimicrobial resistance. The determining may comprise determining movement of the bacteria in three dimensions. With such an arrangement, a more accurate picture of the movement of the bacteria can be obtained.

The determining may comprise determining the movement of individual bacteria. With such an arrangement, there is no requirement for culturing and so the overall time required for the determination of antimicrobial resistance can be reduced.

The arranging may comprise absorbing the bacteria to the coverslip. In such an arrangement, the bacteria can be properly constrained to remain within the evanescent field.

The method may further comprise determining the life status of the bacteria from the vibrations. With such an arrangement, a more complete determination regarding antimicrobial resistance can be made.

The light may be laser light. With such an arrangement, the evanescent field can be reliably produced.

The light may be directed toward the coverslip by a lens and the lens is also arranged to receive light from the coverslip. With such an arrangement, the light can be properly directed on the coverslip and directed toward a detector without the use of two lenses.

The detector may be a quadrant photodiode detector. With such an arrangement, the movement of the bacteria between four different quadrants can be detected in order to give a complete picture of the vibration of the bacteria.

The evanescent field may have a decay length of no more than two hundred nanometres. With such an arrangement, the evanescent field is appropriately sized such that light is not scattered by elements other than bacteria.

The detected light may be light which has been scattered by the bacteria in the bacteria binding volume. With such an arrangement, the bacteria can be analysed with less processing of the data.

The method may further comprise detecting light from the light source, which has undergone total internal reflection and is not scattered by the bacteria, with a second detector. With such an arrangement, there is provided a system for checking the data produced by the first detector in order to provide a more reliable result.

The method may further comprise directing light from a second light source through the coverslip, the light from the second light source undergoing multiple total internal reflections within the coverslip. With such an arrangement, scatterings from multiple bacteria can be detected in order to give a determination of antimicrobial resistance with less time spent using the apparatus.

The method may further comprise directing light from a second light source through an optical waveguide, the light from the light source undergoing multiple total internal reflections within the optical waveguide. With such an arrangement, there is provided an alternative method which does not require the use of a coverslip.

The optical waveguide may be tapered at a point within the evanescent field. With such an embodiment, the apparatus can be more sensitive to the vibration of bacteria in order to give a higher sensitivity for determining antimicrobial resistance.

The determining may be carried out by a processor. With such an arrangement, the determination can be carried out more quickly.

The method may further comprise adding an antimicrobial to the coverslip. With such an arrangement, a determination regarding antimicrobial susceptibility may be made.

The arranging of bacteria on the coverslip may further comprise contacting a portion of the bacteria with an antimicrobial and having a portion of the bacteria uncontacted by the antimicrobial. With such an arrangement, a determination regarding antimicrobial resistance may be made more quickly.

BRIEF DESCRIPTION OF THE DRAWINGS

Embodiments of the invention will now be described with reference to the accompanying drawings, in which.

DETAILED DESCRIPTION OF EMBODIMENT(S)

Figure 1:
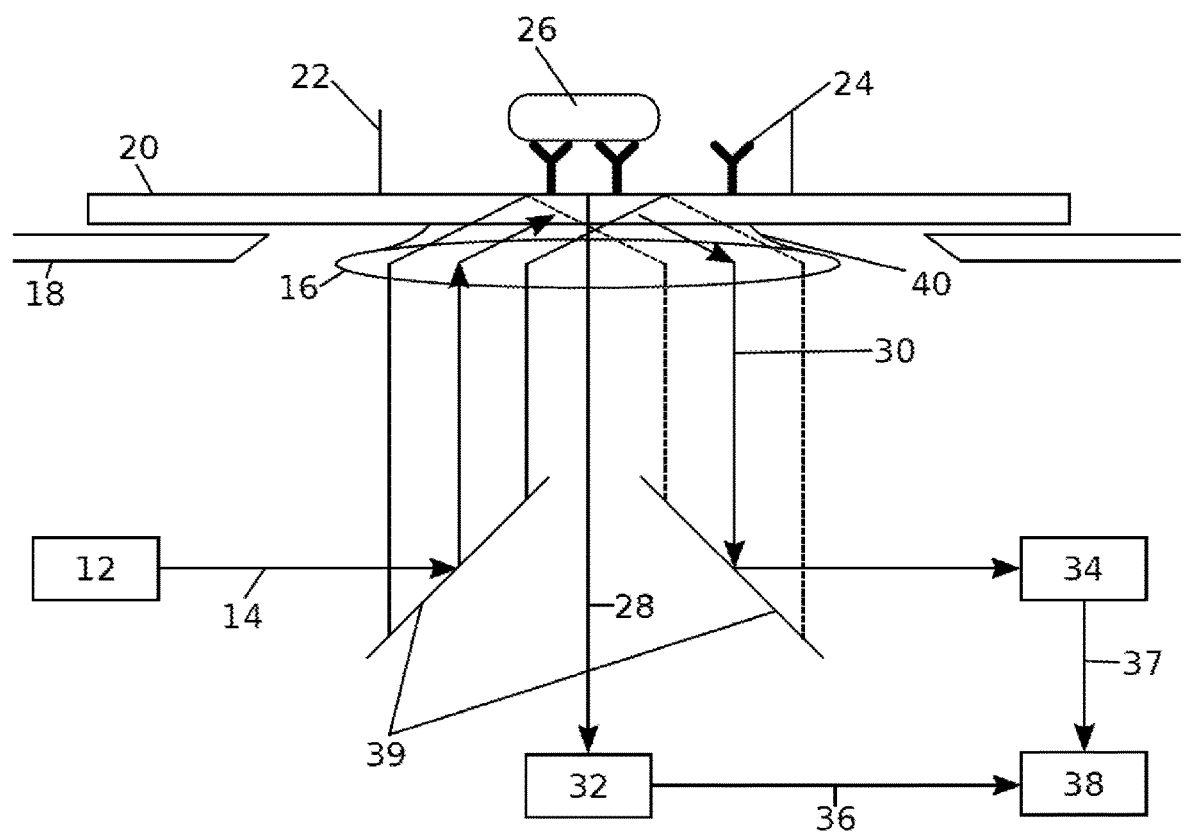
FIG. 1 shows an overall arrangement in accordance with an embodiment of the invention.

FIG. 1 shows an overall system for observing vibrations of bacteria 26 in order to determine antimicrobial resistance.

In an antimicrobial detection system 10, there is a light source 12, which is preferably a laser light source, for example having a wavelength of 561 nanometres. The light source 12 produces a light beam 14 which is then refracted by a lens 16. The lens 16 may be a high numerical aperture lens, combined with immersion oil 40 which refracts the light beam 14 such that the light hits the top surface of a coverslip 20 at an angle greater than the critical angle and is totally internally reflected. It will be understood by a person skilled in the art that the critical angle is a function of the refractive indices of the coverslip 20 and the medium above the coverslip 20.

While the lens 16 having a numerical aperture equal to that of the medium above the lens 16 (approximately 1.33 if the medium is water) would result in total internal reflection and the creation of an evanescent field, the lens 16 having a numerical aperture of 1.4 or greater can produce an evanescent field of appropriate size for the analysis of bacteria.

The coverslip 20 can be a commercially available thin glass coverslip. The coverslip 20 may also be provided separately from the rest of the system 10 and exchangeable for different coverslips having different bacteria and different thicknesses as required by each user. While the coverslip 20 might not be part of the system 10, the system 10 includes a coverslip support 18. The system 10 can therefore be arranged such that the system 10 will function correctly when the coverslip 20 is positioned on the coverslip support 18, without the coverslip 20 being present at the time of the arranging.

The light 14 incident on the top surface of the coverslip 20 forms an evanescent field 22 which forms a circle on the coverslip surface with a Gaussian intensity distribution and a maximum decay length of approximately 200 nanometres. Other configurations are possible for the evanescent field 22; for example the field may be elliptical and have a non-Gaussian intensity distribution. The evanescent field 22 interacts with objects on the surface of the coverslip such as bacteria 26.

Bacteria 26 are elastically bound to the coverslip 20 using antibodies 24 such that the bacteria remain roughly in the centre of the evanescent field 22. The coverslip 20 can be prepared by first being cleaned using ethanol then distilled water and dried in a stream of nitrogen. The surface is then amino-functionalised using ethanolamine hydrochloride, which results in a covering of amino groups covalently bound to the glass to which antibodies 24 can bind. The antibodies 24 used should be those specifically targeted to bind the subject bacteria 26.

The coverslip 20 may form a substrate and the antibodies 24 on the coverslip 20 may form a bacteria binding volume for binding the bacteria 26 in place.

In use, light which has been scattered by the bacteria is then transmitted from the coverslip as scattered light 28. The light passes through the lens 16 and into a first detector 32, which may be a quadrant photodiode detector, which then produces data 36 to provide to a computer system 38.

A quadrant photodetector can monitor both light intensity and the position of peak intensity. Therefore, a quadrant photodetector can be used to determine the distance from the coverslip 22 to the bacteria 26 by the magnitude of the peak intensity of the light detected. The position of the bacteria 26 within the plane of the coverslip 22 can then be determined by the position of the peak intensity detected. Alternatively, an array of photodetectors such as CMOS or CCD may be used in order to determine the position of the bacteria.

Light which has been reflected by the top surface of the coverslip 20 is transmitted from the coverslip as un-scattered light beam 30, which, optionally or alternatively, also passes through the lens 16 and to a second detector 34. The second detector 34 produces second data 37 which are transferred to a computer system such as the computer system 38. As will be understood to the skilled person, either the first detector 32 or the second detector 34 can be omitted from the system or both may be used as required. The second detector 34 can be a quadrant photodetector identical to that of the first detector 32, or can be an array of photodetectors.

In order to direct the light from the light source 12 to the coverslip 20 and from the coverslip 20 to the photodetectors 32, 34, the system can comprise mirrors 39.

The computer system 38 can contain a non-transient computer readable medium and a processor, the non-transient computer readable medium containing instructions for the analysis of the data 36, 37 by the processor in order to provide results to a technician for analysis.

When using the system 10, the bacteria 26 can be arranged on the coverslip 20 using the antibodies 24 and the vibrations of the bacteria 26 can be recorded and stored by the computer system 38. An antimicrobial can then be added to the surface of the coverslip 20 and the subsequent vibration of the bacteria 26 on the coverslip 20 can be recorded by the computer system 38.

If the bacteria 26 are arranged in a liquid environment then the antimicrobial can be added to the liquid environment, either partially or totally. If the antimicrobial is added only to a part of the environment, then the bacteria 26 can be separated spatially on the coverslip 20 so that a group of bacteria 26 uncontacted by the antimicrobial and a group of bacteria 26 contacted by the antimicrobial can be analysed at the same time. Alternatively, a group of bacteria 26 uncontacted by the antimicrobial can be present before the addition of the antimicrobial and the same bacteria 26 can be observed after the addition of the antimicrobial.

If the two groups of bacteria 26 are separated in space (analysed at the same time), then a time saving can be made, whereas if the two groups are separated in time then a greater sample size may be used.

Once the data 36, 37 has been gathered by the computer system 38 it can be processed. In the processing, the level of activity of the bacteria 26 after the addition of the antimicrobial can be compared to the level of activity of the bacteria 26 before the addition of the antimicrobial.

If the level of activity of a bacterium has increased significantly, then it can be assumed that the bacterium has become unbound from the antibody 24 and the result can be discarded. If the level of activity has remained approximately constant, then the bacterium can be considered not to have been affected by the antimicrobial, and if the bacterium has significantly reduced in activity then the bacterium can be deemed to have been affected by the antimicrobial. Antimicrobials can be bactericides or bacteriostats.

The determination of whether a change in a level of activity is significant may be determined by standard statistical testing, such as requiring the change to be greater than 5% to be significant and otherwise determining that the level is approximately unchanged.

The above-analysis can be repeated until a determination can be reached as to whether the bacteria exhibit antimicrobial resistance or not.

Figure 2:
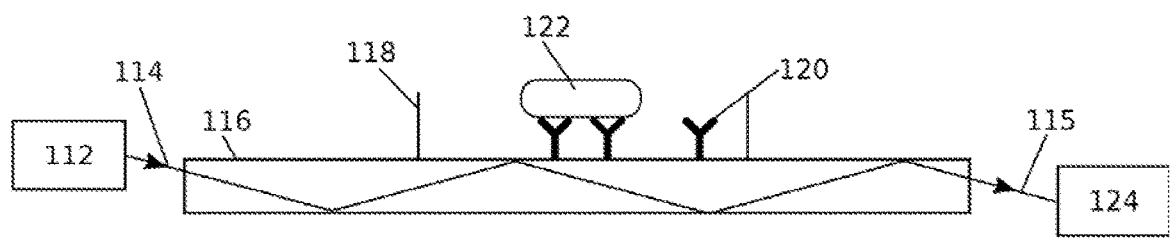
FIG. 2 shows a detailed drawing of a coverslip or waveguide arrangement in accordance with an alternative embodiment of the invention.

FIG. 2 shows a zoomed in image of a coverslip or waveguide arrangement 100 including a coverslip 116, which is functioning as an elongated waveguide. In order to function as a waveguide, the coverslip 116 can have a refractive index greater than 1.6, and optionally be a sapphire coverslip. The coverslip will then function as a waveguide in the apparatus 10 of FIG. 1, in particular in the presence of immersion oil 40.

A second light source 112 provides light 114 which enters coverslip 116 and undergoes multiple total internal reflections. When undergoing the multiple total internal reflections, light 114 creates evanescent field 118, which contains bacteria 122 bound to the coverslip by antibodies 120. As above, the activity of the bacteria 122 within the evanescent field 118 results in scattering of light 114. Light leaves the coverslip 116 as a light beam 115, which is affected by the bacteria 122. A light detector 124 receives the light beam 115.

The second light source 112 can be a laser light source the same as the first light source 12, and the light detector 124 can be a quadrant photodetector or one or more of CMOS OR CCD detectors, which may have the same properties as the first and second detectors 32, 34. Alternatively, a more simple detector measuring only light intensity but not position can be used.

The coverslip arrangement 100 shown in FIG. 2 can be combined with the system 10 of FIG. 1 or may be used on its own, as required. If the coverslip arrangement 100 of FIG. 2 is combined with the system 10 of FIG. 1, then light scattered by the bacteria 122 can be detected by the light detectors of FIG. 1.

In use, the evanescent field produced by the light beam 114 in the coverslip 116 of the coverslip arrangement 100 can encompass multiple bacteria such that light is scattered by more than a single bacterium. Hence, the light beam 115 which exits the coverslip 116 and is detected by light detector 124 contains data produced by interactions related to multiple bacteria 122.

Figure 3:
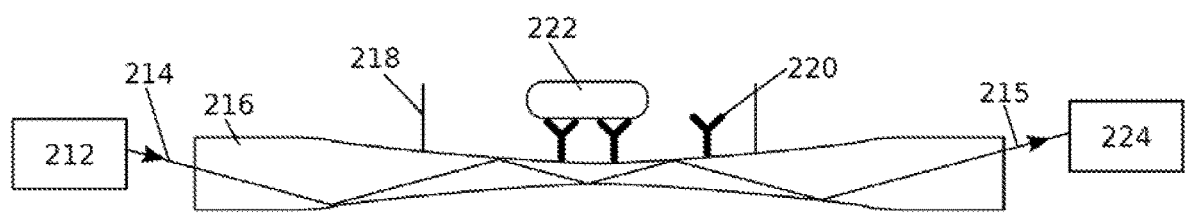
FIG. 3 shows a detailed drawing of a tapered waveguide arrangement in an alternative embodiment of the invention.

A tapered optical waveguide 216 is shown in FIG. 3. The system 200 of FIG. 3 is similar to the system 100 of FIG. 2. In this system, a light source 212 provides a light beam 214 which undergoes multiple total internal reflections within the optical waveguide 216 and creates an evanescent field 218 containing bacteria 222 bound to the optical fibre 216 by antibodies 220. The vibrations of the bacteria 222 results in changes to the light beam 214, which results in a different light beam 215 exiting the optical fibre 216, which is detected by detector 224.

The tapered waveguide 216 differs from the coverslip 116 due to the tapered sides of the tapered waveguide 216. The tapering of the tapered waveguide 216 results in the waveguide being thinner in the middle, such that the overall system can be more sensitive to vibrations within the evanescent field 218. Although the tapering is shown on both sides of the tapered waveguide 216, the tapering may take place on only one side or on both sides. If the tapering takes place on only one side, then this side may be either the top side or the bottom side.

The waveguide 216 should not have any cladding on the outside, as this enables the evanescent field 218 to be exposed such that the bacteria 222 can be arranged within the evanescent field.

The processing for the coverslip arrangements 100 and 200 may be substantially similar and different from the processing for the system 10. In the processing of the data produced from the coverslip arrangements 100 and 200, each dataset contains details of multiple bacteria and aggregated vibrations. The analysis therefore takes a broader overview, with activity calculated for sets of bacteria rather than for individual bacteria. There is therefore less need for repeat readings with the data produced by the coverslip arrangements 100 and 200.

Where the word 'or' appears this is to be construed to mean 'and/or' such that items referred to are not necessarily mutually exclusive and may be used in any appropriate combination.

Although the invention has been described above with reference to one or more preferred embodiments, it will be appreciated that various changes or modifications may be made without departing from the scope of the invention as defined in the appended claims.

What is claimed is:

1. An apparatus comprising:
a light source arranged to cast light toward a transparent coverslip supporting a bacteria binding volume to create an evanescent field, the bacteria binding volume being within the evanescent field;
a detector arranged to receive light from the bacteria binding volume and output data;
a processor programmed to determine a level of vibration of bacteria within the bacteria binding volume in three-dimensions from the output data;
the transparent coverslip arranged to support the bacteria binding volume;
the bacteria binding volume; and
a coverslip support arranged to support the coverslip, the coverslip support being arranged between the light source and the coverslip and having a hole to allow the light cast from the light source to pass to the transparent coverslip;
wherein the evanescent field is created on a surface of the transparent coverslip,
wherein the bacteria binding volume is supported directly on the transparent coverslip; and
wherein the transparent coverslip has no cladding.

2. The apparatus of claim 1, further comprising a lens arranged to direct the light from the light source toward the coverslip.

3. The apparatus of claim 2, wherein the lens has a numerical aperture of at least 1.4.

4. The apparatus of claim 2, wherein the lens is arranged to receive light from the bacteria binding volume.

5. The apparatus of claim 1, wherein the determined vibration is of a single bacterium.

6. The apparatus of claim 1, wherein the detector is arranged to receive light scattered from the bacteria within the bacteria binding volume.

7. The apparatus of claim 6, wherein the apparatus further comprises a second detector, arranged to receive light from the light source having undergone total internal reflection, which is not scattered by the bacteria.

8. The apparatus of claim 1, further comprising a second light source, the second light source being arranged to direct light through the coverslip, the light from the second light source undergoing multiple total internal reflections within the coverslip.

9. The apparatus of claim 8, wherein the coverslip is formed from a dielectric material having a refractive index greater than 1.6.

10. The apparatus of claim 1, further comprising a second light source and wherein the transparent coverslip is arranged to act as an optical waveguide arranged to support the bacteria binding volume, the second light source being arranged to direct light through the optical waveguide.

11. The apparatus of claim 10, wherein the optical waveguide is tapered at a point within the evanescent field.

12. The apparatus of claim 1, wherein the coverslip is separable from the coverslip support.

13. The apparatus of claim 1, wherein the surface of the coverslip where the evanescent field is created contacts the bacteria binding volume.

14. The apparatus of claim 1, wherein the evanescent field is produced by total internal reflection at, at least a surface of the coverslip which contacts the bacteria binding volume.

15. The apparatus of claim 1, wherein the coverslip support directly contacts the coverslip.

16. The apparatus of claim 1, wherein the coverslip is a stand-alone, solid material.

* * * * *